United States Patent
Yegorova et al.

(12)

(10) Patent No.: US 6,399,089 B1
(45) Date of Patent: *Jun. 4, 2002

(54) COMPOSITIONS AND METHODS FOR REGULATING METABOLISM AND BALANCING BODY WEIGHT

(75) Inventors: Inna Yegorova, Northridge; David Jiang, Irvine, both of CA (US)

(73) Assignee: A. Glenn Braswell, Miami, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/571,327

(22) Filed: May 15, 2000

(51) Int. Cl.[7] .................................................. A61K 47/00
(52) U.S. Cl. ....................... 424/439; 424/400; 424/489; 424/725; 514/909; 514/948
(58) Field of Search .................................. 424/400, 439, 424/489, 78.01, 195.1; 514/909, 948

(56) References Cited

U.S. PATENT DOCUMENTS 5,536,506 A * 7/1996 Majeed et al. ............... 424/464
5,911,992 A * 6/1999 Braswell et al. ......... 424/195.1

* cited by examiner

Primary Examiner—Thurman K. Page
Assistant Examiner—Charesse Evans
(74) Attorney, Agent, or Firm—Sierra Patent Group, Ltd.

(57) ABSTRACT

Compositions and methods for balancing body weight by inhibiting re-uptake of serotonin, regulating metabolism, potentiating insulin, and inhibiting lipogenesis, in a mammal. The compositions comprise chromium, fat-free cocoa powder, *Hypericum perforatum* extract, *Garcinia cambogia* extract, *Ginkgo biloba* extract, *Panax ginseng* extract, and quercetin.

60 Claims, No Drawings

COMPOSITIONS AND METHODS FOR REGULATING METABOLISM AND BALANCING BODY WEIGHT

FIELD OF THE INVENTION

The present invention relates to the administration of compositions and methods for balancing body weight by inhibiting re-uptake of serotonin, regulating metabolism, potentiating insulin, and inhibiting lipogenesis, in a mammal.

BACKGROUND OF THE INVENTION

Obesity is a serious heath problem both in the United States as well as world-wide. Results from the National Health and Nutrition Examination Survey III show that one in three Americans are at least twenty percent overweight. Kuczmarski et al., 272 JAMA 205–211 (1994). Other studies have shown that the prevalence of obesity increases three-fold between the ages of 20 and 50, however, this varies for men and women. In particular, the weights of men appear to stabilize after age 50 and then begin to decline around age 60. Women, however, generally continue to gain weight until age 60, and it is not until after age 60 that their weight begins to decline. Kaplan and Sadock, *SYNOPSIS OF PSYCHIATRY* 731 (1998).

Obesity is a condition characterized by excessive accumulation of fat on the body. Obesity can be measured by either body weight or by body mass index (BMI). By convention, obesity is said to be present when body weight exceeds by 20 percent the weight listed in typical height-weight index tables. The other measurement of obesity, BMI, is the amount of fat present in the body and is considered a reliable indication of fatness in non-athletic adults. The BMI may be calculated by using the following formula: BMI equals [body weight in kg] divided by [height in meters]$^2$. In general, a normal BMI is between the range of 20 to 25, whereas the BMI of obese individuals is greater than or equal to 30.

Individuals accumulate fat by eating more calories than are expended as energy. In other words, the intake of energy exceeds its dissipation. Indeed, if fat is to be removed from the body, fewer calories must be consumed or more calories must be expended than are put in. Specifically, the energy content of food is calculated from the heat released by the total combustion of food, which is expressed in kilocalories (kcal or C). Part of the chemical energy released by the oxidation of fuel molecules is dissipated as heat, which in part is used to maintain body temperature. Approximately, 40% of the energy in food is captured in the synthesis of ATP (adenosine triphosphate) from ADP (adenosine diphosphate) and PI (phosphate). Champe and Harvey, *LIPPINCOTT's BIOCHEMISTRY REVIEWS* 298 (1987).

The recommended daily allowance (RDA) for the minimal energy required for an individual has been approximated. Assuming light activity levels typical for most Americans, the recommended dietary energy intake for a 70-kg adult man is approximately 2900 kcal. For a 50-kg adult woman it is about 2100 kcal. The total energy required by an individual is the sum of three energy requiring processes that occur in the body. These include basal metabolism, specific dynamic action, and physical activity. Id., 298–299.

Basal metabolic rate (BMR) is the energy expended by an individual in a resting, postabsorptive state and represents the energy required to carry out the normal body functions. These include, respiration, blood flow, and maintenance of neuromuscular integrity. In an adult, the BMR for men is roughly 1800 kcal and 1300 kcal for women. Approximately, 50% to 70% of the daily energy expenditure in sedentary individuals is attributable to the BMR.

Specific dynamic action, also referred to as diet-induced thermogenesis, is related to the amount of heat produced by the body during the digestion and absorption of food. Specifically, the body heat production of the body increases as much as 30% above the basal level. Over a 24 hour period, the thermogenic response to food may amount to 5% to 10% of the total energy expenditure. Id., 299. In particular, relatively lean individuals may generate up to 40% above the basal level, while obese individuals barely generate a 10% increase above basal level. Murray and Pizzorno, *ENCYCLOPEDIA OF NATURAL MEDICINE* 684 (1998).

The final energy requiring process is physical activity. Indeed, it is physical activity that provides the greatest variation in energy expenditure. The amount of energy consumed during physical activity depends on the time and intensity of the exercise. In general, a sedentary person requires 30% to 50% more than the basal caloric requirement for energy balance, whereas a highly active individual may require 100% or more calories above BMR. Champe et al., supra.

There are a number of physiological and psychological factors that play a role in obesity. Physiological factors include genetic, chemical, physical activity, central nervous system (CNS), and other clinical factors. The presence of numerous forms of inherited obesity make it clear that genetic factors contribute to obesity. About 80% of patients who are obese have a family history of obesity. This fact, however, can be accounted for not only by genetic factors, but also by learned behavior. For example, the individual may have learned to use food as a means of coping with stress and anxiety from their parents. Kaplan et al., supra, 732–736.

A marked decrease in physical activity seems to be a major factor in the rise of obesity as a public health problem. Physical inactivity restricts energy expenditure and may contribute to increased food intake. Although food intake usually increases with increased physical activity, food intake does not necessarily decrease proportionately when physical activity falls below a minimum level. Id. at 735.

The central nervous system, specifically in the lateral and ventromedial hypothalamic areas, adjusts to food intake in response to changing energy requirements, thus maintaining fat stores at a baseline determined by a specific set point. This set point varies from person to person and is dependent upon height and body type. Id. at 733.

There are numerous other clinical factors and disease states that are associated with obesity. For example, Cushing's disease is associated with a characteristic fat distribution, which is often referred as buffalo adiposity. Other disease states associated with obesity include myxedema and adiposogenital dystrophy. Moreover, a drug or treatment regimen may also contribute to obesity. In particular, a prolonged use of serotonergic agonists in the treatment of depression is associated with weight gain. Also, depressed patients are known to have fluctuations in weight. Id.

In addition to the physiological factors that play a crucial role in the development of obesity, there are many psychological factors as well. These may include cultural, family, personality structures, and unconscious conflicts. Thus, individuals who are overweight, may suffer from numerous psychiatric disorders and come from a variety of disturbed backgrounds, and have learned to use over-eating as a means of coping with their problems. Most obese individuals report that they often over-eat when they are emotionally upset. Id. at 734. There are long-range reports supporting the link between emotional factors and obesity. In particular, the reports state that some obese people lose large amounts of weight when they fall in love and gain weight when they lose a loved one. Another study has analyzed the effects of food-use to control mood, concluding that individuals suffering from mild depression often snack on carbohydrates to elevate mood. Lieberman et al., 14(2) *INT. J. EAT. DISORD.* 171–183 (1993).

Many individuals struggling with obesity often have impaired satiety. Satiety is the feeling that results when hunger is satisfied. People generally stop eating at the end of a meal because they have replenished nutrients that had been depleted. Thus, people become hungry again once the nutrients restored at an earlier meal have been used and stored as energy by the body. Obese individuals, however, seem to have an inability to stop eating if food remains available. Kaplan et al., supra, 731.

There are a variety of methods commonly used for treating obesity. These include dietary adjustments such as caloric restriction, exercise regimens, pharmacotherapy, surgery, and psychotherapy. However, there are problems associated with many of these treatments.

The use of human growth (hGH) hormone to treat obesity is described in U.S. Pat. No. 5,597,595. hGH, the most abundant hormone secreted by the pituitary gland, is the primary hormone responsible for growth in mammals, accelerating lipolysis (fat metabolism), and protein synthesis. hGH secretion is markedly decreased in obese individuals. hGH interacts with specific growth hormone receptors, which are widely distributed throughout the body. For example, fat cells (adipocytes) have hGH receptors, and when hGH binds to these receptors, it stimulates the adipocytes to breakdown triglycerides as well as suppresses their ability to take up and accumulate circulating lipids. Administration of hGH needs to be closely monitored, however, as diabetes mellitus may develop in individuals receiving hGH treatment. Diabetes may result because hGH reduces the amount of glucose uptake by cells, thus causing an increase of blood glucose concentration. Not only does this increase in blood glucose levels stimulate the β-cells of the pancreas to secrete extra insulin, but hGH also directly stimulates the β-cells to produce insulin. The combination of these two stimulatory effects so greatly overstimulates insulin secretion that the β-cells literally "burn out." When this occurs, diabetes mellitus may develop. Guyton and Hall; *TEXTBOOK OF MEDICAL PHYSIOLOGY*, 938 (1995).

One of the best ways to induce weight loss is through dieting or caloric restriction, i.e., establish a caloric deficit by bringing intake below output. The most common method of reducing caloric intake is by means of a low calorie diet. There are, however, a couple of common pitfalls to dieting. One is that when the dieter stops the diet and returns to the usual fare, the incentives to overeat are multiplied. Second, many obese people choose novel or bizarre diets. One example of this type of diet is a high-fat/high-protein diet. These diets are known as ketogenic diets because they contain a high level of cholesterol, which facilitates ketosis. Ketosis is associated with nausea, hypotension, and lethargy. Kaplan et al., supra, 735.

Pharmacotherapy may include the administration of drugs that function by increasing serontonin levels in the brain and ultimately controlling appetite. Serotonin (5-hydroxytryptamine, 5HT) is related to several general behaviors such as sleep, emotion, sex, and appetite. The drug Redux® (dexfenfluramine), which is commonly used as a weight control medication, functions by increasing serotonin levels. Specifically, Redux® functions by inhibiting re-uptake of serotonin and at the same time stimulating release of serotonin. Several controlled clinical trials have demonstrated that Redux® can help individuals maintain caloric restriction and a lower body weight for a least a year. It should also be noted that Redux® appears to reduce appetite in obese more than non-obese individuals. Katzung, *BASIC & CLINICAL PHARMACOLOGY* 276 (1998). However, there are some adverse side-effects affiliated with Redux® such as headache, insomnia, and pulmonary hypertension. Id.

Surgical methods that cause malabsorption of food or reduce gastric volume have been widely used in people who are markedly obese. Gastric bypass is a procedure used to make the stomach smaller. In particular, the stomach is reduced by stapling or transecting one of the curvatures of the stomach. The primary objective of reducing the volume of the stomach is to slow the passage of food, thereby limiting the amount of food the individual can intake. Although the results are successful, many adverse side effects result. For example, vomitting, electrolyte imbalance, and obstructions may occur. An alternate surgical procedure is lipectomy, which is the removal of fat. This technique is primarily used for cosmetic purposes, however, and has no real impact on weight loss in the long run. Kaplan et al., supra, 276.

Hence, for all of the reasons detailed above, a better method for facilitating weight lose in obese or overweight individuals that is readily available and cost-efficient is needed. Therefore, the primary objective of the present invention is the administration of a composition that balances body weight and enhances metabolism. One aspect of the present invention is to control appetite and increase satiety by inhibiting re-uptake of serotonin and by increasing serotonin levels. Another aspect of the present invention is to regulate metabolism by administering a composition containing thermogenic substances, which enhances theromgenesis and ultimately aids in weight loss. A further aspect of the present invention is the administration of a composition containing substances that potentiate insulin, which aids in increasing lean body mass. A final aspect of the present invention is to provide a composition that contains substances that inhibit lipogenesis.

SUMMARY OF THE INVENTION

The present invention relates to compositions and methods for facilitating weight loss, enhancing thermogenesis, increasing insulin sensitivity, and inhibiting re-uptake of serotonin. These compositions preferably comprise chromium, fat-free cocoa powder, *Hypericum perforatum* extract, *Garcinia cambogia* extract, *Gingko biloba* extract, *Panax ginseng* extract, and quercetin.

In one preferred embodiment of the present invention, the composition may comprise chromium, wherein the chromium may be chromium picolinate or chromium tripicolinate, a pharmaceutically acceptable carrier, fat-free cocoa powder extracted from the *Theobroma cacao* bean, *Hypericum perforatum* extract comprising 3% hyperforin, *Garcinia cambogia* extract comprising 50% hydroxycitric acid, *Gingko biloba* extract comprising 24% gingko flavonoglycosides and 6% terpenes, and *Panax ginseng* root comprising 25% ginsenosides.

A further preferred embodiment of the present invention is a comprising chromium in an amount from about 90 μg to about 330 μg, fat-free cocoa powder in an amount from about 112.5 mg to about 412.5 mg, *Hypericum perforatum* extract in an amount from about 270 mg to about 990 mg, *Garcinia cambogia* extract in amount from about 112.5 mg to about 412.5 mg, *Ginkgo biloba* extract in an amount from about 54 mg to about 198 mg, *Panax ginseng* extract in an amount from about 36 mg to about 132 mg, and quercetin in an amount from about 22.5 mg to about 82.5 mg. More specifically, the composition may comprise 100 μg chromium, 125 mg fat-free cocoa powder, 300 mg *Hypericum perforatum* extract, 60 mg *Gingko biloba* extract, 125 mg *Garcinia cambogia* extract, 40 mg *Panax ginseng* extract, and 25 mg quercetin.

In another embodiment of the present invention, the composition may be administered to a mammal. Preferably, the mammal is a human. The composition may also be administered orally, preferably two or three times daily.

DETAILED DESCRIPTION OF THE INVENTION

The present invention relates to the administration of compositions and methods for regulating body weight by inhibiting re-uptake of serotonin, regulating metabolism, potentiating insulin, and inhibiting lipogenesis, in a mammal.

It is understood that the present invention is not limited to the particular methodology, protocols, and reagents, etc., described herein, as these may vary. It is also to be understood that the terminology used herein is used for the purpose of describing particular embodiments only, and is not intended to limit the scope of the present invention. It must be noted that as used herein and in the appended claims, the singular forms "a," "an," and "the" include plural reference unless the context clearly dictates otherwise.

Unless defined otherwise, all technical and scientific terms used herein have the same meanings as commonly understood by one of ordinary skill in the art to which this invention belongs. Preferred methods, devices, and materials are described, although any methods and materials similar or equivalent to those described herein can be used in the practice or testing of the present invention. All references cited herein are incorporated by reference herein in their entirety.

Definitions

*Hypericum perforatum*, as described herein will also be referred to as St. John's wort. *Hypericum perforatum* may be standardized to, but is not limited to the following extract formulations: a 0.3% hypericin, water and alcohol extract; a 0.5% hyperforin extract; and a 5% hyperforin extract.

Chromium, as described herein, includes the various forms of chromium available, including but not limited to, chromium picolinate, chromium tripcolinate, chromium chloride, chromium polynicotinate, and chromium-enriched yeast.

A patient, as described herein, includes individuals who require due to a disease state, treatment regimen, or desire, to balance or reduce body weight or enhance metabolism.

One aspect of the present invention is to control appetite and increase satiety by inhibiting re-uptake of serotonin and by increasing serotonin levels. Serotonin is synthesized from the amino acid L-tryptophan by hydroxylation and decarboxylation and is stored at several sites within the body. Approximately, 90% of serotonin is found in the enterochromaffin cells of the gastrointestinal tract. Much of the remaining 10% is found in platelets, while small amounts are found in other tissues, including the brain. Rosenfeld et al., *PHARMACOL*.190–191 (1998). Serotonin is responsible for regulating general behaviors such as sleep, emotions, temperature regulation, the perception of pain, the regulation of blood pressure, and appetite. Substances that suppress appetite through serotonin regulation function generally by blocking re-uptake of serotonin and increasing levels of serotonin in the brain and are refer to as selective serotonin re-uptake inhibitors (SSRI). Indeed, appetite suppression helps overweight or obese individuals trying to reduce body weight, maintain caloric restriction and ultimately lower their body weight. Katzung, supra, 276.

The compositions of the present invention preferably comprise *Hypericum perforatum* (St. John's wort). The most common preparations of St. John's wort make use of the above-ground portion of the plant and most prominently the buds, flowers, and distal leaves. Its constituents include napthodianthrones hypericin, pseudohypericin, protohypericin, protopseudohypericin, and cyclopseudohypericin as well as acylphlorglucinol hyperforin, phenylpropanes, flavonol glycosides, biflavones, tannins and proanthocyanidins, and volatile oils. See Laakmann et al., 31(Suppl) *PHARMACOPYSCHIA*. 54–59 (1998), Nahrstedt et al., 30(Suppl 2) *PHARMACOPYSCHIA*. 129–134 (1997), and Schulz et al., *RATIONAL PHYTOTHERAPY* 52 (1998).

Hyperforin is one of the active ingredients of St. John's wort and studies have demonstrated that it is present in clinically tested St. John's wort formulations at a concentration of 1% to 6%. Chaterjee et al., 31(Suppl) *PHARMACOPSYCHIA*. 7–15 (1998). Importantly, hyperforin functions as a non-specific re-uptake inhibitor of serotonin. Müller et al., 31(Suppl) *PHARMACOPSYCHIA*. 16–21 (1998); see also U.S. Pat. No. 5,911,922. Therefore, the administration of a composition of the present invention that contains St. John's wort aids in appetite suppression and assists in balancing body weight.

Additionally, serotonin has a satiety promoting effect in the body, which aids in the prevention of over-eating. Indeed, agents which increase serotonin levels in the brain would induce satiety. In particular, *Hypericum perforatum* has been shown to enhance satiety and prevent overconsumption of food. See U.S. Pat. No. 5,911,922.

The compositions of the present invention also preferably comprise fat-free cocoa powder and *Garcinia cambogia*, which have also been demonstrated to suppress appetite and thereby encourage weight loss. Cocoa powder extracted from the *Threobroma cacao* bean has been shown to increase serotonin levels in the brain. *PDR FOR HERBAL MEDICINE* 1179–1181 (1998) and Greenwood et al., 240 *AM. J. PHYSIOL*. E72–78 (1981). Additionally, the active ingredient of *Garcinia cambogia*, hydroxycitric acid, has been shown to be effective in suppressing appetite.

Another aspect of the present invention is to regulate or enhance metabolism. This can be accomplished by administering a composition containing thermogenic substances, which will raise an individual's metabolic rate, and thus encourage weight loss. Use of thermogenic agents, especially when an individual is dieting, are of great importance. Caloric restriction during dieting causes the body's metabolic rate to slow. It is this slowing metabolism that promotes the storage of fats. By utilizing a thermogenic enhancing agent, the body maintains a high metabolic rate, which causes the body to burn the caloric intake as energy as opposed to promoting it to be stored as fat. Two of the most widely used thermogenic agents are caffeine and ephedrine.

There are several studies that demonstrate that increasing energy expenditure though enhanced thermogenesis leads to significant weight loss. One study showed that ephedrine increased energy expenditure in rats by 9%, which reduced body weight by 18% and body fat by 50%. Dullo et al., 45(3) *Am. J. CLIN. NUTR.* 564–69 (1987). Another study, it was demonstrated that aspirin potentiated the thermogenic response of ephedrine during a meal eaten by obese women, but not lean women. Horton et al., 15(5) *INT. J. OBES.* 367–74 (1991). These findings suggest that enhanced metabolic rate will increase thermogenesis, leading to fat being burned as energy rather than stored for future use.

The compositions of the present invention preferably comprise fat-free cocoa powder and or *Garcinia cambogia*. Since chocolate contains approximately 0.2% to 0.4% caffeine, chocolate (as well as coffee and tea) would act thermogenically. Preferably, the fat-free cocoa powder is extracted from the *Theobroma cacao* bean. The active ingredient of *Garcinia cambogia*, hydroxycitric acid, is also known as a potent thermogenic agent.

An additional aspect of the present invention comprises potentiating insulin as a means of balancing body weight. Insulin is a polypeptide hormone produced by the pancreatic β cell and is one of the most important hormones coordinating the use of fuels by tissues. Insulin synthesis and release is modulated most importantly by glucose. The β cells are the most important glucose-sensing cells in the body. Ingestion of glucose or a carbohydrate-rich meal leads to a rise in blood glucose, which is a signal for increased insulin secretion. Insulin has numerous mechanisms of action on different tissues. In particular, in adipose tissue, insulin stimulates increased glucose transport into the adipocytes, increases lipogenesis (formation of stored triglycerides) and lipoprotein lipase, and decreases intracellular lipolysis (breakdown of triglycerides for energy). In addition, insulin acts upon muscle cells as well. Specifically, insulin increases glucose transport and glycolysis, increases glycogen deposition (glycogen energy stores), and most importantly, increases protein synthesis. Rosenfeld, supra, 291–292.

The compositions of the present invention preferably comprise chromium picolinate, which is essential to the action of insulin, potentiating its effect. Anderson, 32 *BIOL. TRACE ELEM. RES.* 19–24 (1992) and Mertz, 123(4) *J. NUTR.* 626–633 (1993). Chromium acts to increase insulin sensitivity by improving insulin binding, insulin receptor number, insulin internalization, β-cell sensitivity and insulin receptor enzymes. Anderson 16(5) *J. AM. COLL. NUTR.* 404–10 (1997). Limited research suggests that moderate increases in chromium, in the form of chromium picolinate, may cause weight loss, reduce fat and increase muscle mass. Researchers involved in a 1997 study done in Austria assessed the effects of chromium yeast and chromium picolinate on lean body mass in 36 obese patients during and after weight reduction with a very low calorie diet. During the 26 week treatment period, subjects received either placebo or 200 mcg chromium yeast or 200 mcg chromium picolinate in a double-blind manner. After 26 weeks, chromium picolinate supplemented patients showed increased lean body mass whereas the other treatment groups still had reduced lean body mass. Bahadori et al., 24(5) *ACTA. MED. AUSTRIACA* 185–87 (1997).

In a 1997 study done at the University of Texas at Austin, researchers examined the effects of 400 mcg of chromium and exercise training on young, obese women. The results showed that exercise training combined with chromium nicotinate supplementation resulted in significant weight loss and lowered the insulin response to an oral glucose load. Grant et al., 29(8) *MED. SCI. EXERC.* 992–8 (1997).

The compositions of the present invention also preferably comprise *Panax ginseng*. While ginseng is not considered a potientator of insulin, there is evidence that suggests that ginseng can aid in normalizing blood sugar levels. Ginseng has also been associated with improving glycogen utilization, serum lipids, and increasing protein synthesis. Newall et al., *HERBAL MEDICINES: A GUIDE FOR HEALTH-CARE PROFESSIONALS* 142–143, and 147 (1996).

An additional aspect of the present invention is to inhibit lipogenesis, which also aids in the reduction and balancing of body weight. Lipogenesis primarily occurs in adipocytes. The adipocytes, in response to insulin following a meal high in carbohydrates, hydrolyze triacelyglcerols to fatty acids through a reaction catalyzed by hormone sensitive lipase. Indeed, the rate of glucose uptake by adipocytes, which is regulated by insulin as well as by glucose availability, is a controlling factor in triacylglycerol formation and mobilization. Voet et al., *BIOCHEM.* 735 (1990).

The compositions of the present invention preferably comprise *Garcinia cambogia*, also known as Malabar. Murray et al., supra, 692. The active component of *Garcinia cambogia* for weight management is (−)hydroxycitric acid [(−)HCA]. Hydroxycitric acid, a derivative of citric acid, is found primarily in certain fruits, primarily the tamarind fruit of Southeast Asia. In vitro and in vivo studies suggest that (−)HCA may be helpful in weight loss, because it interferes with the conversion of sugars into fat.

The success of (−)HCA in promoting loss of body fat is linked to its relationship with citrate lyase, an enzyme needed for the formation of acetyl Coenzyme A in the cytoplasm. Acetyl CoA is converted to malonyl CoA, which provides the building blocks for fat synthesis. In the presence of (−)HCA, citrate lyase preferentially combines with the (−)HCA, leaving less of the enzyme available for formation of CoA. Because of this action fat-burning speeds up, appetite is suppressed, metabolic rate increases, stamina and endurance are enhanced, fat production is inhibited and protein is spared.

The compositions of the present invention also preferably comprise mood enhancing agents, which include *Ginkgo biloba* and *Hypericum perforatum*. Individuals who are overweight or obese report that they often over-eat when they are emotionally upset. Kaplan et al., supra at 734. There are long-range reports supporting the link between emotional factors and overeating. In particular, the reports state that some obese people lose large amounts of weight when they fall in love and gain weight when they lose a loved one. Another study has analyzed the effects of food-use to control mood. This study concluded that individuals suffering from mild depression often snack on carbohydrates to elevate mood. Lieberman et al., supra.

*Hypericum perforatum* (St. John's wort) appears to be effective in approximately 55% of patients with mild to moderate depression. On the basis of its antidepressant effect, St. John's wort can also be used for the treatment of anxiety. Other studies show that it can also be effective in the treatment of seasonal affective disorder, reactive depression, and depression with somatic symptoms. See Ernst, 2(1) *PYTOMEDICINE* 67–71 (1995), Hubner et al., 7(Suppl 1)*J. GERIAfR. PSYCH. NEUROL.* S12–S14 (1994), Martinez et al., 7 (Suppl/1) *J. GERIATR. PSYCH. NEUROL.* S29–S33 (1994), and Werth, 15 *DER KASSENARTZ* 64–68 (1989).

Depression is one factor that is extensively used to evaluate the extent of dementia. Many studies involving *Gingko biloba* have noted improvement in this factor along with overall cognitive changes. Indeed, this observation has led to the suggestion that gingko may be effective in treating depression. One study has directly evaluated this benefit. Forty depressed patients above the age of fifty who showed incomplete response to tricyclic or tetracyclic antidepressants were given adjuvant treatment with either placebo or *Ginkgo biloba* extract at 80 mg three times a day. The patients in the gingko treatment group demonstrated significant improved outcomes when compared with the placebo group. Schubert et al., 3 *GENIATR. FORSCH.* 45–53 (1993).

The compositions of the present invention preferably comprise quercetin. Quercetin is a flavonoid and is a natural constituent of nearly all plants. Quercetin is the most abundant of all the flavonoids and is found in a number of common foods, including onions, apples, tea, berries, and cabbage family vegetables. It is also found in a number of medicinal herbs, including ginkgo, St. John's wort, eucalyptus, and elderberry.

Flavonoids have a variety of functions. Certain flavonoids, including quercetin, have aldose reductase inhibitor activity, i.e., they inhibit the enzyme that converts glucose to sorbitol. Also, quercetin protects cells in the body from damage by free radicals. Heart disease and high cholesterol may be caused by free radical damage to blood vessels, and therefore, it may be suggested that quercetin protects against heart attacks and strokes.

As discussed in detail above, in one aspect of the invention, the novel compositions of the present invention preferably comprise chromium; fat-free cocoa powder; *Hypericum perforatum* extract; *Garcinia cambogia* extract; *Ginkgo biloba* extract; *Panax ginseng* extract; and quercetin. Chromium, fat-free cocoa powder, *Hypericum perforatum* extract, *Garcinia cambogia* extract, *Ginkgo biloba* extract, *Panax ginseng* extract and quercetin are available commercially, in bulk and wholesale, from suppliers well known to those skilled in the art. For instance, chromium may be obtained from Ava Health PO Box 730, Grove City, Ohio 43123-0730 and BASF, Inc. Additionally, *Gingko biloba, Hypericum perforatum* and *Panax ginseng* may be obtained from, e.g., Barefoot Doctors Apothecary, 111 East Ann Street, Ann Arbor, Mich. 48104. *Garcinia cambogia* may be obtained from, e.g., Sabinsa Corporation, 121 Ethel Road West, Piscataway, N.J. 08854.

Another aspect of the present invention relates to compositions and methods for balancing body weight by inhibiting the re-uptake of serotonin regulating metabolism, potentiating insulin, and inhibiting lipogenesis, comprising administering to the mammal a composition comprising: chromium; fat-free cocoa powder; *Hypericum perforatum* extract; *Garcinia cambogia* extract; *Ginkgo biloba* extract; *Panax ginseng* extract; and quercetin.

According to one embodiment of the invention, the present composition is formulated for oral administration. Any dosage form may be employed for providing the patient with a dosage of the present compositions. Dosage forms include tablets, capsules, dispersions, suspensions, solutions, capsules, transdermal delivery systems, etc. Tablets and capsules represent the most advantageous oral dosage unit form. Any method known to those of ordinary skill in the art may be used to prepare capsules, tablets, or other dosage formulations. Tablets or capsules can be coated by methods well known to those of ordinary skill in the art.

According to one aspect of the invention a composition is provided comprising a pharmaceutically acceptable combination of the composition and at least one carrier. Pharmaceutically acceptable carriers for inclusion into the present compositions include carriers most suitable for combination with lipid-based drugs such as diluents, excipients and the like which enhance its oral administration. Suitable carriers include, but are not limited to, sugars, starches, cellulose and derivatives thereof, wetting agents, lubricants such as sodium lauryl sulfate, stabilizers, tabletting agents, antioxidants, preservatives, coloring agents and flavoring agents. Pharmaceutically acceptable carriers include binding agents such as pregelatinized maize starch, polyvinylpryrrolidone or hydroxypropyl methycellulose; binders or fillers such as lactose, pentosan, microcrystalline cellulose or calcium hydrogen phosphate; lubricants such as magnesium stearate, talc or silica; disintegrants such as potato starch or sodium starch; or wetting agents such as sodium lauryl sulfate. Reference may be made to *REMINGTON'S PHARMACEUTICAL SCIENCES, 17TH ED.*, 1985, for other carriers that would be suitable for combination with the present compositions. As will be appreciated, the pharmaceutical carriers used to prepare compositions in accordance with the present invention will depend on the administrable form to be used.

Another embodiment of the invention involves administering the composition of the present invention to a human in one or more tablets as a material dietary supplement. In yet another embodiment of the invention, the composition is administered to a human as a pharmaceutical composition. The administration of the composition is preferably in accordance with a predetermined regimen, which may be at least once daily and over an extended period of time as a chronic treatment, and could last for one year or more, including the life of the host. The dosage administered will depend upon administration frequency, the blood level of the components of the composition desired, other concurrent therapeutic treatments, the condition's severity, whether the treatment is for prophylaxis or therapy, the patient's age, the degree of weight loss desired, and the like.

Other objectives, features and advantages of the present invention will become apparent from the following specific examples. The specific examples, while indicating specific embodiments of the invention, are provided by way of illustration only. Accordingly, the present invention also includes those various changes and modifications within the spirit and scope of the invention that may become apparent to those skilled in the art from this detailed description.

EXAMPLE 1

Composition 1
A composition of the following formulation was prepared in tablet form by standard methods known to those skilled in the art:

| | |
|---|---|
| Fat-free Cocoa Powder | 125 mg |
| *Hypericum perforatum* extract | 10 mg |
| *Garcinia cambogia* extract | 125 mg |
| *Gingko biloba* extract | 60 mg |
| Chromium | 100 µg |
| *Panax ginseng* extract | 40 mg |
| Quercetin | 25 mg |

Three tablets per day is the recommended dosage for an average weight adult human (70-kg).

Clinical Studies:

A study of the effect of a dietary supplement comprising chromium, fat-free cocoa powder, *Hypericum perforatum* extract, *Garcinia cambogia* extract, *Ginkgo biloba* extract, *Panax ginseng* extract and quercetin, on insulin levels, dietary intake, body mass index, and physical activity, is conducted over a six-month period. A statistical analysis is performed to compare the resulting insulin levels, dietary intake, body mass index, and physical activity of the test and a control (placebo) group to measure the improvement in insulin sensitivity, dietary intake, body mass index, and physical activity from administration of the test preparation.

Sixty men having a body mass index of greater than 30 are selected for inclusion in the statistical study. Two weeks prior to the start of the study, each subject completes a one-week dietary intake record and is interviewed by a Registered Dietitian to calculate each individual's daily energy requirement. After this, weight calculations, physical activity levels, and dietary intake levels are determined, and baseline blood samples are drawn on two separate days, then the subjects are randomly assigned to one of two treatment groups: the group receiving the test tablets (Composition 1) or the group receiving matching placebo tablets. Both groups continue on their normal diet and incorporate three tablets of either the Composition 1 or placebo in their daily diet. Each group documents their daily dietary intake, their level of physical activity, and their weight for the period of the study.

The effects of supplementing the diet with the above composition are evaluated for insulin sensitivity, dietary intake, body mass index, and physical activity using multiple linear regression analysis and a standard students t-test. In each analysis, the baseline value of the outcome variable is included in the model as a covariant. Treatment by covariant interaction effects is tested by the method outlined by Weigel and Narvaez, 12 *CONTROLLED CLINCAL TRIALS* 378–394 (1991). In the absence of significant interaction effects, the interaction terms are removed from the model. Regression model assumptions of normality and homogeneity residual variance are evaluated by inspection of plots of residuals versus plots of predicted values. Temporal outset of effects is detected sequentially by testing for the presence of significant treatment effects at 18, 12, and 6 weeks, proceeding to the earlier time in sequence only when significant effects have been identified at each later time period. In addition, one-way analysis of variance is compared only when differences exist between groups concerning nutrient intake, physical activity, and body mass index at each time point. Changes from the baseline within each group are evaluated using paired t-tests. Additionally, analysis of variance is performed on all baseline measurements and measurable subject characteristics to assess homogeneity between groups. All statistical procedures are conducted using the Statistical Analysis System (SAS Institute Inc., Cary, N.C.) using an alpha level of 0.05 for all statistical tests.

A statistically significant increase in physical activity, and a statistically significant decrease in dietary intake and body mass index are observed in the treated subjects upon completion of the study, but not in the control subjects. A statistically significant increase in insulin sensitivity are observed in the treated subjects upon completion of the study, but not in the control subjects.

EXAMPLE 2

A study of the effect of the composition comprising chromium, fat-free cocoa powder, *Hypericum perforatum* extract, *Garcinia cambogia* extract, *Ginkgo biloba* extract, *Panax ginseng* extract and quercetin, on brain serotonin levels, is conducted over a six-month period. A statistical analysis is performed to compare the resulting mood and brain serotonin levels of a test group and a control (placebo) group to determine if a significant improvement in mood and brain serotonin levels results from administration of the test preparation.

Sixty men are selected for inclusion in the statistical study. Two weeks prior to the start of the study each subject completes a one-week emotional record and is interviewed by a licensed psychologist to show each individual's overall emotional well being. After this, emotional well being is again determined, baseline cerebrospinal fluid (CSF) samples are drawn on two separate days, and the subjects are randomly assigned to one of two treatment groups: the group receiving the test capsules or the group receiving placebo capsules. Both groups continue on their normal diet and incorporate three tablets of either Composition 1 or the placebo in their daily diet. Each group documents their emotional well-being via conventional methods for the period of the study.

The effects of the dietary supplementation on brain serotonin levels is evaluated. Levels of serotonin in the brain are tested by the method outlined by Issa et al., 52(3) *PSYCH. RES.* 237–249 (1994). The testing method utilizes a technological advance in high performance liquid chromatography with electrochemical detection and combines it with a multivariate statistical analysis study of biogenic amine concentrations in CSF. This approach enables the study of the interactions of several metabolites of each of the three major neurotransmitter pathways (dopaminergic, noradrenergic, and serotonergic) to test existing brain serotonin levels. Twenty biogenic amines, their metabolites, and other compounds from 30 subjects given the Composition 1, and 30 given the placebo, are simultaneously measured using a recently developed technique of gradient high performance liquid chromatography coupled with a 16-channel electrochemical array detector. After covariation for storage time, results comparing the two groups may be performed utilizing a stepwise discriminant function analysis.

A statistically significant increase in emotional well-being and brain serotonin levels are observed in the subjects given the test composition upon completion of the study, but not in the control subjects.

The invention has been described in detail with particular reference to preferred embodiment thereof. However, it will be appreciated that those skilled in the art, upon consideration of this disclosure may make variations and modifications within the spirit and scope of the invention.

The disclosure of all publications cited above are expressly incorporated by reference in their entireties to the same extent as if each were incorporated by reference individually.

We claim:

1. A composition for facilitating weight lose, enhancing thermogenesis, increasing insulin sensitivity, and inhibiting re-uptake of serotonin comprising: chromium; fat-free cocoa powder; *Hypericum perforatum* extract; *Garcinia cambogia* extract; *Ginkgo biloba* extract; *Panax ginseng* extract; and quercetin.

2. The composition of claim 1, wherein said chromium comprises chromium picolinate.

3. The composition of claim 1, wherein said chromium comprises chromium tripicolinate.

4. The composition of claim 1, further comprising a pharmaceutically acceptable carrier.

5. The composition of claim 1, wherein said fat-free cocoa powder is extracted from the *Theobroma cacao* bean.

6. The composition of claim 1, wherein said *Hypericum perforatum* extract comprises 3% hyperforin.

7. The composition of claim 1, wherein said *Garcinia cambogia* extract comprises 50% hydroxycitric acid.

8. The composition of claim 1, wherein said *Ginkgo biloba* extract comprises 24% ginkgo flavonoglycosides and 6% terpenes.

9. The composition of claim 1, wherein said *Panax ginseng* extract is extracted from *Panax ginseng* root.

10. The composition of claim 1, wherein said *Panax ginseng* extract comprises 25% ginsenosides.

11. The composition of claim 1, wherein said chromium contained in the composition is from about 90 µg to about 330 µg.

12. The composition of claim 1, wherein said fat-free cocoa powder contained in the composition is from about 112.5 mg to about 412.5 mg.

13. The composition of claim 1, wherein said of *Hypericum perforatum* extract contained in the composition is from about 270 mg to about 990 mg.

14. The composition of claim 1, wherein said *Garcinia cambogia* extract contained in the composition is from about 112.5 mg to about 412.5 mg.

15. The composition of claim 1, wherein said *Ginkgo biloba* extract contained in the composition is from about 54 mg to about 198 mg.

16. The composition of claim 1, wherein said *Panax ginseng* extract contained in the composition is from about 36 mg to about 132 mg.

17. The composition of claim 1, wherein said quercetin contained in the composition from about 22.5 mg to about 82.5 mg.

18. The composition of claim 1, comprising:
   100 µg chromium;
   125 mg fat-free cocoa powder;
   300 mg *Hypericum peroratum* extract;
   125 mg *Garcinia cambogia* extract;
   60 mg *Ginkgo biloba* extract;
   40 mg *Panax ginseng* extract; and
   25 mg quercetin.

19. A method of improving facilitating weight loss, enhancing thermogenesis, increasing insulin sensitivity, and inhibiting re-uptake of serotonin in a mammal comprising:
   administering to said mammal a composition comprising chromium, fat-free cocoa powder, *Hypericum perforatum* extract, *Garcinia cambogia* extract, *Ginkgo biloba* extract, *Panax ginseng* extract, and quercetin.

20. The method of claim 19, wherein said mammal is a human.

21. The method of claim 19, wherein said chromium comprises chromium picolinate.

22. The method of claim 19, wherein said chromium comprises chromium tripicolinate.

23. The method of claim 19, wherein said composition further comprises a pharmaceutically acceptable carrier.

24. The method of claim 19, wherein said fat-free cocoa powder is extracted from the *Theobroma cacao* bean.

25. The method of claim 19, wherein said *Hypericum perforatum* extract comprises 3% hyperforin.

26. The method of claim 19, wherein said *Garcinia cambogia* extract comprises 50% hydroxycitric acid.

27. The method of claim 19, wherein said *Ginkgo biloba* extract comprises 24% ginkgo flavonoglycosides and 6% terpenes.

28. The method of claim 19, wherein said source of *Panax ginseng* extract is extracted from *Panax ginseng* root.

29. The method of claim 19, wherein said *Panax ginseng* comprises 25% ginsenosides.

30. The method of claim 19, wherein said chromium contained in the composition is from about 90 µg to about 330 µg.

31. The method of claim 19, wherein said fat-free cocoa powder contained in the composition is from about 112.5 mg to about 412.5 mg.

32. The method of claim 19, wherein said *Hypericum perforatum* extract contained in the composition is from about 270 mg to about 990 mg.

33. The method of claim 19, said *Garcinia cambogia* extract contained in the composition is from about 112.5 mg to about 412.5 mg.

34. The method of claim 19, said *Ginkgo biloba* extract is contained in the composition from about 54 mg to about 198 mg.

35. The method of claim 19, wherein said *Panax ginseng* extract is contained in the composition from about 36 mg to about 132 mg.

36. The method of claim 19, said quercetin is contained in the composition from about 22.5 mg to about 82.5 mg.

37. The method of claim 19, wherein said composition comprises:
   100 µg chromium;
   125 mg fat-free cocoa powder;
   300 mg *Hypericum perforatum* extract;
   125 mg *Garcinia cambogia* extract;
   60 mg *Ginkgo biloba* extract;
   40 mg *Panax ginseng* extract; and
   25 mg quercetin.

38. The method of claim 37, wherein said composition is administered 2 to 3 times daily.

39. The method of claim 38, wherein said administration is oral administration.

40. A method of regulating body metabolism by balancing body weight in a mammal comprising: administering to said mammal a composition comprising, chromium, fat-free cocoa powder, *Hypericum perforatum* extract, *Garcinia cambogia* extract, *Ginkgo biloba* extract, *Panax ginseng* extract, and quercetin.

41. The method of claim 40, wherein said mammal is a human.

42. The method of claim 40, wherein said chromium comprises chromium picolinate.

43. The method of claim 40, wherein said chromium comprises chromium tripicolinate.

44. The method of claim 40, wherein said composition further comprises a pharmaceutically acceptable carrier.

45. The method of claim 40, wherein said fat-free cocoa powder is extracted from the *Theobroma cacao* bean.

46. The method of claim 40, wherein said *Hypericum perforatum* extract comprises 3% hyperforin.

47. The method of claim 40, wherein said *Garcinia cambogia* extract comprises 50% hydroxycitric acid.

48. The method of claim 40, wherein said *Ginkgo biloba* extract comprises 24% ginkgo flavonoglycosides and 6% terpenes.

49. The method of claim 40, wherein said *Panax ginseng* extract is extracted from *Panax ginseng* root.

50. The method of claim 40, wherein said *Panax ginseng* comprises 25% ginsenosides.

51. The method of claim 40, wherein said chromium contained in the composition is from about 90 µg to about 330 µg.

52. The method of claim 40, wherein said fat-free cocoa powder contained in the composition is from about 112.5 mg to about 412.5 mg.

53. The method of claim 40, wherein said *Hypericum perforatum* extract contained in the composition is from about 270 mg to about 990 mg.

54. The method of claim 40, said *Garcinia cambogia* extract contained in the composition is from about 112.5 mg to about 412.5 mg.

55. The method of claim 40, said *Ginkgo biloba* extract is contained in the composition from about 54 mg to about 198 mg.

56. The method of claim 40, wherein said *Panax ginseng* extract is contained in the composition from about 36 mg to about 132 mg.

57. The method of claim 40, said quercetin is contained in the composition from about 22.5 mg to about 82.5 mg.

58. The method of claim 40, wherein said composition comprises:

100 µg chromium;

125 mg fat-free cocoa powder;

300 mg *Hypericum perforatum* extract;

125 mg *Garcinia cambogia* extract;

60 mg *Ginkgo biloba* extract;

40 mg *Panax ginseng* extract; and 25 mg quercetin.

59. The method of claim 58, wherein said composition is administered 2 to 3 times daily.

60. The method of claim 59, wherein said administration is oral administration.

* * * * *